(12) United States Patent
Temple

(10) Patent No.: US 9,603,963 B2
(45) Date of Patent: Mar. 28, 2017

(54) METHOD AND APPARATUS FOR TREATING INDUSTRIAL GAS STREAMS AND BIOLOGICAL FOULING

(76) Inventor: Stephen R. Temple, Santa Cruz, CA (US)

(*) Notice: Subject to any disclaimer, the term of this patent is extended or adjusted under 35 U.S.C. 154(b) by 477 days.

(21) Appl. No.: 12/901,454

(22) Filed: Oct. 8, 2010

(65) Prior Publication Data

US 2012/0087827 A1   Apr. 12, 2012

(51) Int. Cl.
*A61L 9/00* (2006.01)
*A61L 9/14* (2006.01)

(52) U.S. Cl.
CPC ................... *A61L 9/145* (2013.01)

(58) Field of Classification Search
CPC ........................................ A61L 9/145
USPC .............................. 422/4; 423/238
See application file for complete search history.

(56) References Cited

U.S. PATENT DOCUMENTS

| | | | | |
|---|---|---|---|---|
| 4,455,287 A | * | 6/1984 | Primack et al. | 423/576.6 |
| 2004/0115112 A1 | * | 6/2004 | Stoltz et al. | 423/245.1 |
| 2009/0104099 A1 | * | 4/2009 | Au-Yeung et al. | 423/238 |
| 2010/0183738 A1 | * | 7/2010 | Kramer | A01N 37/16 424/616 |

OTHER PUBLICATIONS

EPA Reregistration Eligibility Decision (RED)2,2-dibromo-3-nitrilopropionamide (DBNPA), EPA 738-R-94-026, Sep. 1994.

* cited by examiner

*Primary Examiner* — Kevin Joyner
(74) *Attorney, Agent, or Firm* — Owens Tarabichi LLP

(57) ABSTRACT

Methods and apparatuses are described for contacting an oxidizing solution such as an aqueous hydrogen peroxide composition of hydrogen peroxide, at least one additive that catalyzes the decomposition of the hydrogen peroxide into hydroxyl radicals, and a biocide with an atmospheric effluent containing odorous and/or noxious components. These components are absorbed by the aqueous hydrogen peroxide composition to produce an atmospheric effluent having reduced amounts of the odorous and/or noxious components. Various methods are described for adding the hydrogen peroxide, the decomposition additive, and the biocide.

21 Claims, 6 Drawing Sheets

METHOD AND APPARATUS FOR TREATING INDUSTRIAL GAS STREAMS AND BIOLOGICAL FOULING

BACKGROUND

Background of the Invention

This invention relates to the treatment of industrial gas streams. More specifically, the invention relates to the treatment of industrial gas streams, such as a gas stream produced in a rendering process, to remove odorous and noxious component through the use of a gas scrubber system and to reduce biological fouling through the use of a biocide in the gas scrubber system.

Description of Related Art

In the processing of poultry, beef, fish, or other food, as well as in secondary processing (e.g., rendering), a large volume of organic material is processed that can generate large quantities of odiferous and noxious gases including organic sulfides, thiols, amines, alcohols, inorganic sulfides, ammonia, and simple carboxylic acids. These compounds are usually the result of biological action on the organic materials being processed. The odors produced are offensive and can travel significant distances to surrounding real estate. In other industries, such as chemical processing, paint production, wastewater treatment, etc., noxious compounds, such as volatile organic compounds (VOCs), are produced and are subject to environmental air quality regulations.

These gases are usually collected and sent to a scrubber system where they are removed from the gas phase. In such a scrubber system, the collected gases from the process are evacuated into a gas/liquid contactor where they are contacted by a liquid stream or scrubbing solution that is recirculated in the scrubber to absorb the odiferous and noxious gas compounds.

During operation of these scrubbing systems, the scrubbing solution will quickly saturate with the offensive gases and lose its absorbing potential. For example, as the scrubbing solution saturates with gases, particularly nitrogen-bearing gases (e.g., ammonia), the pH of the scrubbing solution will rise proportionally. This marked increase in pH reduces the solubility of the gases in the scrubbing solution and may cause them to flash to the atmosphere or off-gas. Further, at this point, the scrubbing solution has an intense disagreeable odor. Accordingly, additives may be added to the scrubbing solution to reduce its odor content. Ultimately, the scrubbing solution is either dumped to a wastewater treatment facility, or a portion of the scrubbing solution is sent to a wastewater facility and fresh makeup water is added to account for the difference.

In addition, as the water media recirculates in the system, there is an increase in the concentration of bacteria and protein and, accordingly, an increase in various types of biological growth, including the growth of bacteria, fungus, or yeast. This biological growth is typically referred to as biological fouling or biofouling and can cause problems within the system. For example, biofouling in the scrubber may begin to plug any packing used in the scrubber resulting in the obstruction of the flow of both the gas and liquid through the packing. This increases the pressure drop in the scrubber, and increases the gas flow rate through the scrubber thereby reducing the overall gas/liquid contact efficiency and removal efficiency of odorous and noxious components from the gas stream. Further, in those systems that utilize oxidizers to remove odorous and noxious components from the gas stream, the presence of biological activity and biofouling in the liquid streams will reduce the concentration of such oxidizers, thereby making less available for removal of the odorous and noxious components.

Accordingly, there exists a need in the art for a treatment process that has a sufficiently high electronegative potential to reduce substantially all odor and/or noxious compounds to simple, soluble, reduced-odor/noxious, or odor/noxious-free compounds and that reduces or prevents biofouling in the system. This treatment process would offer even greater advance in the art if the process could also eliminate or greatly reduce the high cost of treating the scrubber water effluent in the wastewater treatment process.

SUMMARY OF THE INVENTION

In general, the present invention relates to chemical compositions and systems, including processes and equipment for removing odorous and/or noxious components from an atmospheric effluent. In one embodiment, the chemical composition includes an oxidizer capable of oxidizing the odorous and/or noxious components. In another embodiment, the chemical composition includes an aqueous hydrogen peroxide composition of hydrogen peroxide, an additive that catalyzes the decomposition of hydrogen peroxide into hydroxyl radicals, and a biocide that treats biological fouling. When contacted with the atmospheric effluent, the oxidizer or aqueous hydrogen peroxide composition oxidizes the odor and/or noxious components to produce an atmospheric effluent having reduced amounts of the odor component and/or noxious component and, in some embodiments, a non-odor offensive, environmentally acceptable byproduct. In one embodiment, the addition of the biocide to the chemical composition prevents biological fouling. In other embodiments, the addition of the biocide to the chemical composition removes existing biological fouling.

A method is described for removing at least one of an odor component and a noxious component from an atmospheric effluent. In one embodiment, the atmospheric effluent is contacted with a solution comprising an oxidizer. In another embodiment, the atmospheric effluent is contacted with an aqueous hydrogen peroxide composition including hydrogen peroxide and at least one additive that catalyzes the decomposition of the hydrogen peroxide to produce hydroxyl free radicals. The odorous and/or noxious component in the atmospheric effluent is absorbed by the oxidizer solution or the aqueous hydrogen peroxide composition and oxidized. In another embodiment, the method further comprises contacting the gas and liquid in a counter-current fashion. In another embodiment, the oxidizer solution or the aqueous hydrogen peroxide composition can be collected after contacting the gas in a tank and recycled via a recycle stream to again contact the gas. In this embodiment, additional oxidizer or additional hydrogen peroxide and decomposition additive may be added to the recycle stream as required or based upon measurement of a given solution parameter that is used to indicated whether additional oxidizer or additional hydrogen peroxide or decomposition additive is required. In some embodiments, the measurement of the solution parameter may be done continuously, periodically, or manually. In some embodiments, the addition of the oxidizer or other additives may be done automatically using a flow control valve based upon the measured value of the solution parameter to provide a more precise addition rate of these components and better control of the solution composition compared to a simple on/off valve.

In some embodiments, the decomposition additive comprises a metal-based compound, such as a ferrous or ferric salt, such as ferrous sulfate or ferric sulfate. In other embodiments, the decomposition additive comprises ozone, which may be added concurrently with the hydrogen peroxide to the liquid stream to improve contacting between the ozone gas and the hydrogen peroxide in the liquid stream.

In one embodiment, the method for removing an odorous or noxious component from a gas stream comprises adding hydrogen peroxide, a hydrogen peroxide decomposition additive, and a chelating agent to a liquid stream; contacting a gas stream comprising at least one odorous or noxious component with the liquid stream; and absorbing at least a portion of said odorous or noxious component in the gas stream into the liquid stream. The chelating agent is added to increase the solubility of the hydrogen peroxide decomposition additive. In some embodiments, the chelating agent allows the pH of the liquid stream to be controlled at a higher value than the liquid stream would otherwise have under similar operating conditions without the chelating agent. This may improve removal of certain odorous or noxious components. In some embodiments, the decomposition additive comprises a ferrous salt, such as ferrous sulfate, and the chelating agent comprises aminopolycarboxylates, such as nitrilotriacetic acid and hydroxyethyliminodiacetic acid; N-heteroxcyclic carboxylates, such as picolinic acid; polyhydroxy aromatics, such as gallic acid; or other compounds, such as rhodizonic acid, tetrahydroxy-1,4-quinone, and hexaketocyclohexane. In other embodiments, the chelating agent comprises methylglycinediacetate or trisodium methylglycinediacetate (available as TRILON M from BASF Corporation). In other embodiments, methylglycinediacetate or trisodium methylglycinediacetate can be mixed with a source of ferric ion, such as a ferric salt solution, to produce a ferric chelate, ferric methylglycinediacetate, as described in U.S. Pat. No. 6,960,330 to Cox, the entirety of which is incorporated herein by reference.

In some embodiments the pH of chemical composition or the liquid stream may be controlled at a select pH by adding acid or base directly to the liquid stream or to a tank that collects the liquid stream after contacting the gas. In other embodiments, the acid or base may be mixed with the decomposition additive before addition to the chemical composition or the liquid stream or the tank that collects the liquid stream after contacting the gas.

Other advantages of the present invention will become apparent from the following detailed description taken in conjunction with the accompanying drawings that illustrate, by way of example, the principles of the invention.

DETAILED DESCRIPTION OF THE INVENTION

Figure 1:
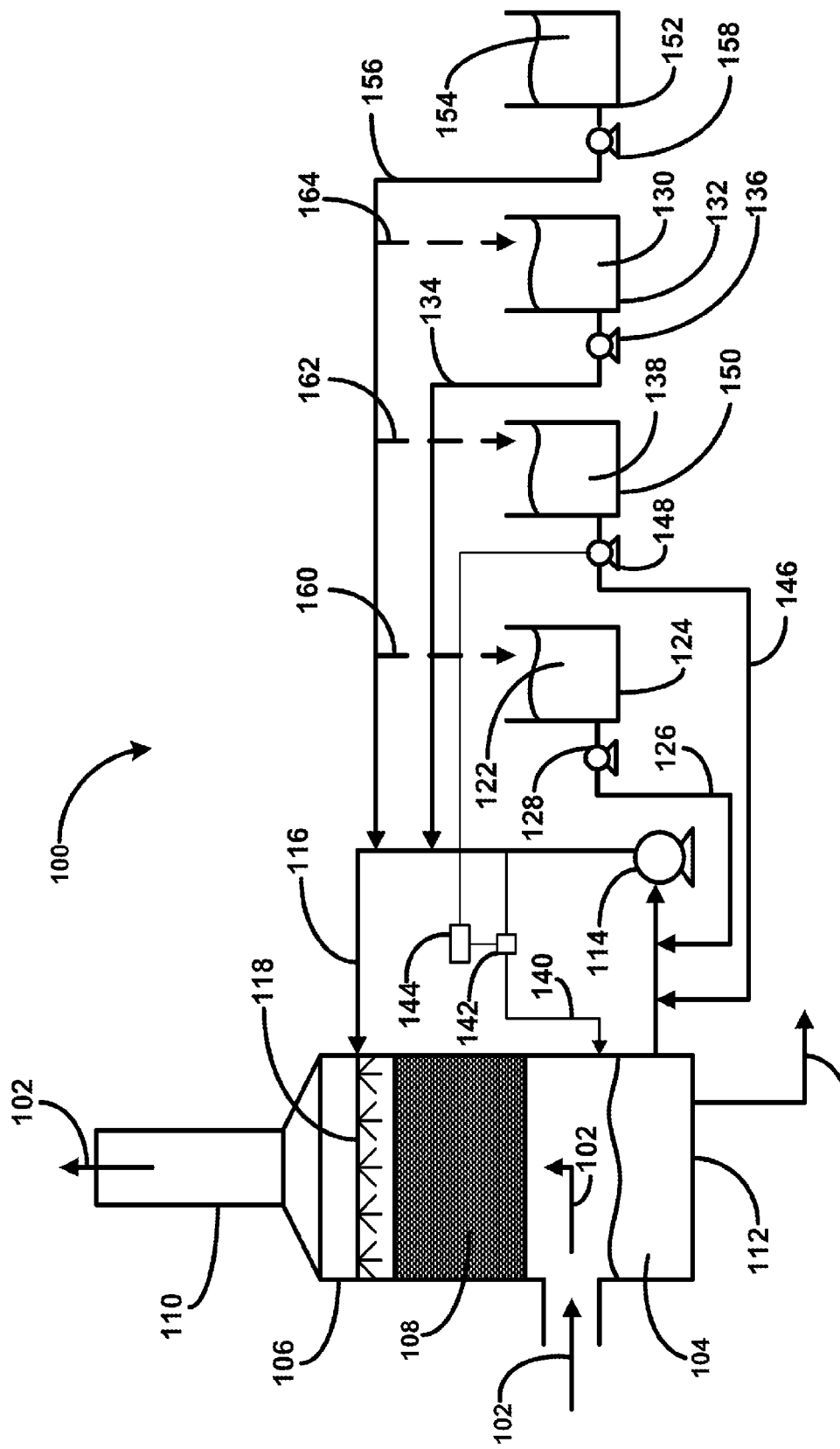
FIG. 1 shows a process flow diagram of one embodiment of a process for removing an odor and/or noxious component from a gas stream and for reducing biological fouling in the process.

Various embodiments of the present invention are described below with reference to the accompanying drawings. To facilitate explanation, the various embodiments will be described primarily in the context of a particular embodiment, namely, a wet scrubber system comprising a packed column as the gas/liquid contactor. However, it should be understood that the invention can be applied to a wide variety of applications, and it is intended to cover alternatives, modifications, and equivalents as may be included within the spirit and scope of the invention as defined by the appended claims. Accordingly, the following description is exemplary in that several embodiments are described (e.g., by use of the terms "preferably" or "for example"), but this description should not be viewed as limiting or as setting forth the only embodiments of the invention, as the invention encompasses other embodiments not specifically recited in this description. Further, the use of the term "invention" throughout this description is used broadly and is not intended to mean that any particular portion of the description is the only manner in which the invention may be made or used.

In general, the present invention uses a liquid stream or scrubbing solution comprising at least one chemical component that is an oxidizer to oxidize odorous and/or noxious components that have been absorbed from a gas stream into the scrubbing solution. In some embodiments, additives may also be added to the scrubbing solution, including, for example, acid or base to control the pH of the scrubbing solution, additives to enhance the effectiveness of the oxidizer (e.g., when using hydrogen peroxide as the oxidizer the additive may be a hydrogen peroxide decomposition additive that catalyzes the decomposition of hydrogen peroxide to hydroxyl free radicals; chelating agents that, for example, increase the solubility of the hydrogen peroxide decomposition additive; wetting agents; and dispersants) and a biocide to reduce or eliminate biofouling in the gas/liquid contactor, including, for example, the packing. It should be appreciated that any chemical added to the scrubbing solution may be referred to as an additive.

In one embodiment, the scrubbing solution comprises an aqueous hydrogen peroxide composition of hydrogen peroxide, at least one additive that serves to catalyze the rapid decomposition of the hydrogen peroxide into hydroxyl radicals, and a biocide. When contacted with a gas stream containing odorous and/or noxious components, the hydroxyl radicals oxidize the odorous and noxious components to a non-odor offensive, environmentally acceptable byproduct. The byproduct in combination with the aqueous hydrogen peroxide composition forms a liquid effluent that provides charge neutralizing and adsorption species that, in addition, aids in treatment of wastewater effluents.

As can be seen in Table 1 below, the hydroxyl radical is known in the art as the second most electronegative species, second only to fluorine, and is significantly higher in oxidation potential than other compounds known in the art. The highly electronegative hydroxyl radical is, therefore, capable of a much greater decomposition of odor-causing molecules than any composition known in the art. As such, in some embodiments, the hydroxyl radical is used to oxidize the absorbed odorous and/or noxious components, as opposed to, or in addition to, hydrogen peroxide itself. Accordingly, in one embodiment, at least a portion of the hydrogen peroxide in the scrubbing solution used to contact a gas stream containing odorous and/or noxious components is decomposed to produce hydroxyl radical, which, in turn, oxidizes the absorbed odorous and/or noxious components.

TABLE 1

| Oxidizer | Oxidation Potential (Volts) |
| --- | --- |
| fluorine | 3.0 |
| hydroxyl radical | 2.8 |
| ozone | 2.1 |
| hydrogen peroxide | 1.8 |
| potassium permanganate | 1.7 |
| hypobromous acid | 1.6 |
| chlorine dioxide | 1.5 |
| chlorine | 1.4 |

Therefore, in some embodiments, although not necessary, it is desirable to drive the hydrogen peroxide decomposition reaction to produce predominantly hydroxyl radicals to act in the oxidation of the odorous and/or noxious components in the gaseous effluent. It should be appreciated that neither all of the hydrogen peroxide needs to be decomposed to hydroxyl radicals nor does the decomposition need to result in only the production of hydroxyl radicals. In some embodiments, it is sufficient that a portion of the hydrogen peroxide decomposes to produce at least some quantity of hydroxyl radicals. Moreover, in some embodiments, the decomposition of hydrogen peroxide may produce some diatomic oxygen, which also has an oxidation potential.

As noted above, in another embodiment, one additive that may be used in the scrubbing solution is a biocide to reduce or prevent biofouling and related operating problems. Biofouling in the scrubber may begin to plug any packing used in the scrubber resulting in the obstruction of the flow of both the gas and the scrubbing solution through the packing. This increases the pressure drop in the scrubber, and increases the gas flow rate through the scrubber thereby reducing the overall gas/liquid contact efficiency and removal efficiency of odorous and noxious components from the gas stream. In other scrubbers that do not utilize packing, such as spray towers or AC cross flow scrubbers, a biocide can be used to keep the surfaces of the scrubber and spray nozzles free of biofilms that can slough-off the surfaces and impede spray nozzle and scrubber performance. Further, in those embodiments that utilize oxidizers to remove odorous and noxious components from the gas stream, the presence of biological activity and biofouling in the scrubbing solution will reduce the concentration of such oxidizers, thereby making less available for removal of the odorous and noxious components. The use of a biocide in the scrubbing solution may reduce or prevent biofouling by reducing or stopping biological growth of, for example, bacteria, fungus, or yeast.

FIG. 1 shows a diagram of one embodiment of a process for removing an odorous and/or noxious component from a gas stream and for treating biofouling in the process. In this embodiment, a wet scrubber system 100 is used to contact a gas stream 102 comprising an odorous and/or noxious component with a scrubbing solution 104 comprising an aqueous solution of hydrogen peroxide, at least one additive that catalyzes the decomposition of the hydrogen peroxide to hydroxyl radicals, and a biocide to remove certain odorous and/no noxious components from the gas stream 102.

In this embodiment, the gas stream 102 (as represented by the arrows) comprising at least one or more odorous and/or noxious components enters a wet scrubber 106. The gas stream 102 may be from a food processing process, rendering process, or other industrial process that produces gaseous odoriferous and/or noxious components that can be collected and fed to a scrubber. In this embodiment, the wet scrubber comprises packing 108, although it should be appreciated that any type of gas/liquid contactor may be used, including a spray tower with or without packing. The gas stream 102 enters the wet scrubber 106 and passes through the packing 108 and eventually through a stack or outlet duct 110 where the gas stream 102 is discharged to the atmosphere.

The wet scrubber 106 also comprises a sump 112 that holds the scrubbing solution 104. In some embodiments, the sump 112 is integral to the scrubber 106; however, the sump 112 may also be separate from the scrubber 106. The scrubbing solution 104 is pumped by a pump 114 from the sump 112 through a recycle line 116 to a bank of spray nozzles 118 where is it discharged into the packing 108. It should be appreciated that a wide variety of pumps may be used. The pump should be chosen to provide sufficient power to move fluid at the mass flow rate required by the particular scrubber. It should also resist chemical attach by the scrubbing solution 104 and any additives present in the scrubbing solution 104. For certain applications, it may be desirable to use specific types of pumps. For example, when using the pump to introduce ozone or other gaseous catalysts, a pump capable of introducing a gas into a liquid stream could be used, such as a regenerative turbine pump. It should also be appreciated that the scrubbing solution 104 can be discharged onto the packing in any manner known in the art.

Once discharged onto the packing 108, the scrubbing solution 104 flows in a counter-current fashion to the direction of the gas stream 102. The packing 108 acts to facilitate contact between the gas stream 102 and the scrubbing solution 104 to allow for the absorption of one or more odorous and/or noxious components from the gas stream 102 into the scrubbing solution 104. Accordingly, the gas stream 102 that exits through the stack or outlet duct 110 has a reduced concentration of odorous and/nor noxious components.

After passing through the packing 108, the scrubbing solution 104 is collected in the sump 112 and recycled back to the top of the packing 108. The sump 112 also has a discharge line 120 that allows either the entire scrubbing solution 104 or a portion thereof to be discharged, for example, to a wastewater treatment system (not shown). One of skill in the art will appreciate that water may be added to the sump 112 depending upon the amount of scrubbing solution 104 discharged to maintain the water balance in the process and a desired level in the sump 112.

The scrubbing solution 104 comprises hydrogen peroxide, at least one additive that catalyzes the decomposition of at least a portion of the hydrogen peroxide to hydroxyl radicals, and a biocide. In one embodiment, the additive that catalyzes the decomposition of hydrogen peroxide is used to produce predominantly hydroxyl free radicals such that the scrubbing solution 104 has a relatively high concentration of hydroxyl radicals compared to a hydrogen peroxide solution upon discharge from the spray nozzles 118.

In the scrubber 106, and particularly in the packing 108, the gas stream 102 and the scrubbing solution 104 comprising hydroxyl free radicals contact each other. During this contact, odorous and/or noxious components in the gas stream 102 are absorbed by the scrubbing solution 104 and are oxidized to produce a substantially non-odor-offensive, environmentally acceptable byproduct. The oxidation of these components enhances the absorption capacity of the scrubbing solution 104 to allow additional odorous and/or noxious components to be absorbed. Dependent on the oxidation of the odorous and/or noxious component, the scrubbing solution 104 may contain byproduct that is soluble in the scrubbing solution 104 or that may adsorb onto semi-colloidal particles formed in the scrubbing solution 104.

It should be appreciated that at the start of the process the contents of the sump 112 may be essentially makeup water until the process has completed several cycles in which the scrubbing solution 104 has been contacted the gas stream 102. However, during steady-state operation, various components are added to the scrubbing solution to maintain its absorption capacity. Specifically, as the scrubbing solution 104 is pumped from the sump 112 to the spray nozzles 118, various chemical components are added to the scrubbing solution 104.

Aqueous hydrogen peroxide and any other additives, including the biocide, are added to the scrubbing solution 104 in the recycle line 116. The hydrogen peroxide 122 is delivered from a source container 124 through a feed line 126 into the recycle line 116 using a pump 128. It should be appreciated that the hydrogen peroxide 122 is added upstream of the recycle pump 114, although, as discussed below, the hydrogen peroxide 122 may be added downstream of the recycle pump 114. In some embodiments in which the hydrogen peroxide is added downstream of the recycle pump 114, any decomposition additive can be added downstream of the point where the hydrogen peroxide 122 is added. Although it should be appreciated that the decomposition additive can be added upstream or downstream of the hydrogen peroxide.

The concentration of hydrogen peroxide 122 in the source container 124 should be chosen to allow safe handling given the equipment in use and to provide sufficient concentration for the needs of the scrubber. Although the concentration of hydrogen peroxide in the source container 124 may be selected within a wide range, specific embodiments will range between about 35% to about 50% by weight in an aqueous solution as these ranges are currently industrially available and legally transportable. In a preferred embodiment, the concentration is about 50% by weight in aqueous solution. In other embodiments, the concentration is about 70% by weight in aqueous solution.

The decomposition additive 130, or a mixture of multiple decomposition additives, is delivered from a source container 132 through a feed line 134 into the recycle line 116 using a pump 136. Upon the addition of the decomposition additive 130 to the recycle line 116 and its inherent mixing with the scrubbing solution 104 in the recycle line 116, the decomposition of at least a portion of the hydrogen peroxide to hydroxyl radicals is catalyzed and occurs within the recycle line 116. The scrubbing solution 104 comprising the hydroxyl radicals is then delivered to the scrubber 106 and the packing 108 through the spray nozzles 118. In one embodiment, the decomposition additive produces predominantly hydroxyl radicals; however, as noted above, it is not necessary that all of the hydrogen peroxide decompose to hydroxyl radicals or that the decomposition itself only produce hydroxyl radicals. Depending upon the amount of hydroxyl radicals produced, which can be determined based upon the removal efficiency of the odorous and/or noxious components from the gas stream 102, the rate and amount of decomposition additive delivered to the recycle line 116 can be adjusted.

Since the decomposition of at least a portion of the hydrogen peroxide to hydroxyl radicals occurs upon the addition of the decomposition additive 130, it is preferable to add the decomposition additive 130 downstream of the recycle pump 114. This reduces wear on the recycle pump 114 from the decomposition product of hydrogen peroxide, e.g., the hydroxyl radicals. However, it should be appreciated that the decomposition additive 130 may be added upstream of the recycle pump 114.

In some embodiments, the decomposition additive is a catalyst that catalyzes the decomposition of hydrogen peroxide to hydroxyl free radicals. Generally, the catalyst selected relative to the gas stream being treated and the specific gaseous components to be removed so as to generate an aqueous hydrogen peroxide composition having an optimal concentration of hydroxyl free radicals. The catalyst is also selected with a view toward safety and effectiveness. Obviously, the concentration of the catalyst used will vary depending upon the particular catalyst chosen. Typically, the catalyst will be delivered using an aqueous solution as described above, although for some catalysts, such as ozone and certain of the group VII elements (discussed further below), a direct gaseous addition will be necessary.

In one embodiment, the decomposition additive used is ferrous sulfate. In aqueous media, ferrous ion decomposes hydrogen peroxide in the following manner:

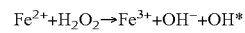
$Fe^{2+}+H_2O_2 \rightarrow Fe^{3+}+OH^-+OH^*$

It should be appreciated that the solubility limit of the catalyst presents an upper bound on concentration of the catalyst in the source container 132. In the case of ferrous sulfate, the concentration may be selected within a wide range with specific embodiments within the range between about 20% to about 38% by weight in aqueous solution. In a preferred embodiment the concentration of ferrous sulfate is about 38% by weight in aqueous solution. In this embodiment, the aqueous hydrogen peroxide composition may be added as a 50% by weight hydrogen peroxide solution in its source container.

The ratio by weight of the hydrogen peroxide solution to the ferrous sulfate, based on a 50% by weight hydrogen peroxide solution and a 38% by weight ferrous sulfate solution should be within the range between about 1:1 to about 100:1, within the range between about 2:1 to about 50:1, or within the range between about 5:1 to about 15:1. The higher the ferrous sulfate ratio the more the decomposition reaction is driven to producing hydroxyl free radicals. The ratio can be as high as one part 50% by weight hydrogen peroxide solution to ten parts 38% ferrous sulfate solution, but an extreme amount of heat is generated. While this amount of heat may be acceptable in some settings, it may not be desirable in others.

It should be appreciated that the use of highly electronegative hydroxyl radicals is capable of a much greater decomposition of odor-causing molecules than any composition known in the art. Further, the use of some of the decomposition additives, particularly, ferrous sulfate, not only reduces the hydrogen peroxide into the hydroxyl radicals but also introduces a semi-colloidal substrate into the aqueous media that is capable of effectively adsorbing odorous and/or noxious compounds.

Other additives that act as catalysts, other than ferrous sulfate, may be used alone or in combination with ferrous sulfate. In one embodiment, the catalytic additive may be any element chosen from elements in groups 3B, 4B, 5B, 6B, 7B, 8B, 1B, and 2B of the Periodic Table of Elements and may include combinations thereof. It will be readily apparent to one of normal skill in the art that the additive(s) selected from these elements would be chosen based upon cost, speed of reaction, and environmental impact. Among these elements, iron and its conjugates are the cheapest, most readily available, and of the lowest environmental impact.

The "d" block transition elements, characterized by the "d" electrons in their valence shell, and combinations thereof, may also be used. For example, the additive may be cobalt. In one embodiment, the aqueous hydrogen peroxide composition may be formed using an amount of cobalt within the range between about 0.5% wt/wt % to about 1% wt/wt % of the total aqueous hydrogen peroxide composition. Or, the amount of cobalt may be between about 0.5% wt/wt % to about 1% wt/wt % of a solution comprised of cobalt and a 50% by weight hydrogen peroxide solution. In another embodiment, the additive may be any element selected from elements in Group 7A of the Periodic Table of Elements and combinations thereof, for example, fluorine.

In one embodiment, the decomposition additive may be ozone. Using ozone as the additive to catalyze the decomposition of the hydrogen peroxide provides numerous advantages. In particular, using ozone allows for operation at higher pH because the ozone is not as solubility limited at higher pH compared to the decomposition additives that comprise metals. As discussed below, the solubility of a metal-based decomposition additive typically decreases at higher pH, but a chelating agent may be used to enhance its solubility. The use of ozone, however, may displace the need to use a chelating agent in combination with a metal-based decomposition, thereby allowing operation at higher pHs. As noted above, operation at higher pH provides the aqueous hydrogen peroxide composition with a greater capacity to absorb acidic odorous and noxious components in the gas stream to be treated, thereby increasing the removal efficiency of the process. Accordingly, when using ozone, because solubility of a metal-based catalytic additive is not an issue, the pH of the aqueous hydrogen peroxide composition may be increased. The particular pH used in operation can be determined as discussed above and is based upon factors such as the type and concentration of the odorous and/or noxious components in the gas stream and the operating conditions of the scrubber. Generally, it should be appreciated that virtually any pH above, for example, 5.0, may be used.

When using ozone very poor gas transfer to liquid media has been observed in the art. As part of the present invention, use of a regenerative turbine pump, for example, a Burks regenerative turbine pump manufactured by Burks Manufacturing, can be used as the recycle pump to provide sufficient to excellent mixing of the ozone with the scrubbing solution in the recycle line. Referring back to FIG. 1, such a regenerative turbine pump can be used as the recycle pump 114 in the recycle line 116. In this case, the hydrogen peroxide is added as shown in FIG. 1 upstream of, or on the vacuum side, of the regenerative turbine pump. An ozone/air mixture can then be added to an inlet port pre-built on the vacuum side of the regenerative turbine pump. The resulting liquid discharged from the regenerative turbine pump provides a well mixed stream. In particular, pressurizing the discharge side of the pump to a minimum of 100 psi by using a pinch valve (not shown) gives excellent gas transfer of the ozone to the liquid media in the recycle line. It will be appreciated that this pinch valve may also be controlled using the same control system that regulates the addition of the other additives shown in FIG. 1. It should be appreciated that in some embodiments, the ozone may be added either upstream or downstream of the recycle pump or in any other manner to maximize the transfer of the ozone into the liquid phase and the decomposition of the hydrogen peroxide.

More particularly, as the scrubbing solution, enriched with hydrogen peroxide (due to the addition of hydrogen peroxide from the hydrogen peroxide source container 124), enters the vacuum side of the regenerative turbine pump, the air/ozone mixture is introduced through a pre-machined air port. Intense shear is developed inside the regenerative turbine pump that breaks the ozone/air mixture into microbubbles entrained in the scrubbing solution. The discharge from the regenerative turbine pump is pressurized to approximately 100 psi through a pinch valve assembly, ensuring solubilization of the ozone into the scrubbing solution enriched with hydrogen peroxide, but noting that lower pressures may be used. This allows for the efficient decomposition of the hydrogen peroxide by the ozone into hydroxyl radicals.

The system and process of the embodiment of FIG. 1 may also include a pH control loop to measure the pH of the scrubbing solution 104 in the recycle line 116 and, in response, to regulate the addition of an acid or base 138 into the recycle line 116 to maintain the pH of the scrubbing solution 104 within a preferred pH range.

In such an embodiment, a sidestream 140 of scrubbing solution 104 is taken from the recycle line 116 and passed by a pH probe 142 and then returned to the scrubber 106. The pH probe 142 measures the pH of this sidestream 140 and communicates the measured pH to a pH controller 144. The pH controller 144 then regulates, as needed, the addition of an acid or base 138 from an acid or base source container 146 into the recycle line 116 through feed line 148 using a pump 150. In one embodiment, the acid or base 138 is added upstream of the recycle pump 114. However, it may also be added to the sidestream 140 or downstream of the recycle pump 114. In another embodiment, the acid or base 138 can be added directly to the sump 112.

Through the addition of acid or base using the pH control loop, the pH of the scrubbing solution 104 in the recycle line 116 can be maintained at a level that maximizes the decomposition of the hydrogen peroxide by the decomposition additive that catalyze such decomposition. This, in turn, allows the removal of the odorous and/or noxious component from the gas stream to be optimized. One of skill in the art will appreciate that the optimal pH to be used will be dependent upon the particular gaseous components to be removed and oxidized and their respective properties and concentration in the gas stream 102, as well as the composition of the scrubbing solution 104 and operating conditions of the scrubber 106. For example, in removing hydrogen sulfide, its solubility is pH dependent and increases with increasing pH above about pH 5 to about pH 9.5. Accordingly, this solubility property needs to be taken into account in selecting an operating pH of the scrubbing solution. Additionally, the solubility of the decomposition additive, particularly a metal-based additive (discussed below), relative to the pH of the scrubbing solution needs to be taken into account. Typically, metal-based additives are less soluble at higher pH, so that the pH may need to be controlled at a lower level to maintain an adequate concentration of such an additive in solution to catalyze the decomposition of the hydrogen peroxide.

In some embodiments, the scrubbing solution 104 may include additional additives, including wetting agents, dispersant polymers, and/or chelating agents (discussed further below). Addition of these additives would be made similar to the addition of the additive for catalyzing the decomposition of the hydrogen peroxide discussed above. Thus, there may be separate source containers to enable the regulated delivery of these additional additives in aqueous form to the recycle line 116. Preferably, these additional additives are added on the downstream side of the recycle pump 114; however, these additives could be added at other locations, including, for example, anywhere along the recycle line 116 or directly to the sump 112. Additionally, some or all of these other additives may be mixed together and delivered from a single source container. Alternatively, any one or more of these additives may be provided together with one or more other additives. For example, the hydrogen peroxide in its source container 124 may contain any one or more chemically compatible (e.g., resistant to oxidation) additives such as certain chelating agents and/or wetting agents. Of course, the additives may also be provided with the decomposition additive 130 from its source container 132 and/or from a source container 150 containing acid or base 138.

In one embodiment, a nonionic wetting agent may be added to the scrubber or to the scrubbing solution to enhance its activity by allowing further penetration of the oxidizing agent into crevices of bacterial forms of odorous and/or noxious components. While the exact mechanism is not known, it is believed that certain nonionic surfactants, i.e., wetting agents, assist in the degradation of bacterial cell walls allowing the scrubbing solution to more readily kill the bacteria in the medium.

Preferred wetting agents are octylphenols, ethylene oxide block copolymers, propylene oxide block copolymers, and combinations thereof. The determining factors for wetting agent choice is organic loading of the effluent, i.e., the level of proteins or starches in the effluent, cleanliness of the system being treated, i.e., the amount of deposits and slime on the surfaces of the scrubber tank and packing, as well as need for defoaming capabilities.

In one embodiment, the wetting agent, as 100% active material, is present in an amount up to about 10% by weight of the scrubbing solution (in the scrubber or as additives to recycle line), an amount up to about 5% by weight of the scrubbing solution, or an amount up to about 1% by weight of the scrubbing solution.

In another embodiment, a low molecular weight dispersant polymer may be added to the scrubber or to the scrubbing solution in order to prevent iron and other particle agglomeration in the aqueous media as well as to prevent iron and organic deposition in lower liquid flow areas. In one embodiment, the average molecular weight of these low molecular weight dispersants is within the range between about 1,000 to about 22,000 or within the range between about 1,000 to about 9,000. These low molecular weight dispersants may be, but are not limited to, homopolymers of acrylic acid, methacrylic acid, acrylamide, copolymers and terpolymers acrylates, methacrylates, acrylamide, AMPS (2-acrylamido-2-methyl propane sulfonic acid), and combinations thereof. For example, a dispersant resistant to oxidation may be desirable in situations where sulfur-based compounds that are formed as a result of operation at higher pHs and interaction with a metal-based decomposition additive in which insoluble agglomerations, such as zinc sulfate, are formed.

The low molecular weight dispersant polymer is added on a weight percent basis (i.e., wt/wt % on the total composition weight of the aqueous hydrogen peroxide composition in the scrubber or as additives to a scrubber sidestream). In one embodiment, the percentage of the low molecular weight dispersant in the scrubbing solution is within the range between about 0.5% active wt/wt % to about 10% active wt/wt % of the total scrubbing solution, within the range between about 0.5% active wt/wt % to about 5% active wt/wt % of the total scrubbing solution, or within the range between about 0.5% active wt/wt % to about 2% active wt/wt % of the total scrubbing solution.

In another embodiment, a chelating agent may be added to the scrubbing solution. As earlier discussed, a semicolloidal metal complex may form during the oxidation process, and in some instances, the development of this colloidal metal complex is undesirable. A chelating agent may be added to prevent the formation of metal hydroxides or other insoluble metal complexes. In one embodiment, the chelating agents may be organic acids such as gluconic acids, glycolic acids, lactic acids, and combinations thereof. It will be appreciated that a large number of chelating agents may also be used and their selection readily apparent to those of skill in the art; however, the chelating agent should not be of such potent chelating ability as to prevent the availability of the metal complex for decomposition purposes.

A chelating agent may also be added to enhance the solubility of the decomposition additive or catalyst. This may, in some embodiments, allows for operation at higher pH. As noted above, higher pH increases removal of the odorous and/or noxious components in the gas compared to lower pH operation. It should be appreciated, however, that a chelating agent may be used to enhance the solubility of the decomposition additive in some embodiments where increasing the pH may not be necessary.

Generally, chelating agents can be selected based upon the particular decomposition additive being used. For example, chelating agents known in the art may be used to increase the solubility of metal-based decomposition additives, such as ferrous ion and other metal complexes. In addition, ferric ($Fe^{3+}$) ion may be used as the decomposition additive to decompose hydrogen peroxide to produce hydroxyl radicals, and chelating agents may be added to increase the solubility of the ferric ion, thereby increasing the production of hydroxyl free radicals and allowing for operation at a higher pH. Chemical Treatment of Pesticide Wastes—Evaluation of Fe(III) Chelates for Catalytic Hydrogen Peroxide Oxidation of 2,4-D at Circumneutral pH, Sun et al., J. Agric. Food Chem., 1992, 40, 322-327, which is incorporated by reference herein, describes several chelating agents that may be used to solubilize ferric ion. Such chelating agents that showed "high" catalytic activity and that may be used in the present invention include: aminopolycarboxylates, such as nitrilotriacetic acid and hydroxyethyliminodiacetic acid; N-heteroxcyclic carboxylates, such as picolinic acid; polyhydroxy aromatics, such as gallic acid; and other compounds, such as rhodizonic acid, tetrahydroxy-1,4-quinone, and hexaketocyclohexane. These chelating agents may be used separately. However, it may be possible to use mixtures of these chelating agents as well. In other embodiments, the chelating agent comprises methylglycinediacetate or trisodium methylglycinediacetate (available as TRILON M from BASF Corporation) or methylglycinediacetic acid.

It should be appreciated that the chelating agent and the decomposition additive, such as ferrous ion or ferric ion (which may be added, for example, as ferric sulfate) may be mixed before use to allow for chelation. For example, referring to FIG. 1, the chelating agent and the ferric ion may be chelated prior to placing such a mixture in the source container 132 for the decomposition additive. In this case, the selection of the decomposition additive and chelating agent can be based upon the specific application or particular gaseous components to be removed and the desired operating pH. By mixing the decomposition additive and the chelating agent prior to use, this mixture is essentially "tailor-made" and is ready for immediate use in the particular application at issue. In fact, this mixture can be prepared remote from the facility where it will be used and shipped to that facility for immediate use. In some embodiments, methylglycinediacetate or trisodium methylglycinediacetate can be mixed with a source of ferric ion, such as a ferric salt solution, to produce a ferric chelate, ferric methylglycinediacetate, as described in U.S. Pat. No. 6,960,330 to Cox, the entirety of which is incorporated herein by reference.

Alternatively, the decomposition additive and the chelating agent may be added separately to the decomposition additive source container 132, thereby allowing for in-situ chelation in the source container 132. In this case, consideration must be given to the rate at which this solution is added to the recycle line 116 to provide sufficient time for chelation to occur. One of skill in the art will appreciate the conditions necessary to chelate, including use of the proper pH, which may be, for example, pH 6. Alternatively still, the chelating agent may be added through the use of a separate source container (not shown) in a manner similar to that of the decomposition additive source container 132. Further, the use of a separate source container for the chelating agent may be used to dispense the chelating agent into the recycle line 116 either upstream or downstream of the recycle pump 114; however, it is preferable to dispense the chelating agent into the recycle line 116 as closely as possible to the point where the decomposition additive is added to the recycle line 116.

As noted above, use of a chelating agent to increase the solubility of the decomposition additive (for example metal-based additives and, in particular, ferrous or ferric ions) allows for operation at a higher pH in the aqueous hydrogen peroxide composition that is fed to the scrubber. Operation at higher pH increases the capacity of the aqueous hydrogen peroxide composition to absorb additional acidic gases, thereby increasing the removal efficiency of the process. It should be appreciated that the specific pH used will be dependent upon the particular gaseous components to be removed from the gas stream and, correspondingly, may include a wide range of pHs. In some embodiments, it may be desirable to not change the operating pH significantly or at all upon the addition of a chelating agent.

The system and process of the embodiment of FIG. 1 also includes a source container 152 that delivers the biocide 154 into the scrubber 106. In one embodiment, the biocide 154 is added to the scrubber 106 through a feed line 156 to the recycle line 116 using a pump 158. In this case, the biocide 154 may be added upstream or downstream of the recycle pump 114. In either case, the biocide 154 will enter the scrubber 106 with the scrubbing solution 104. The biocide can be added continuously or semi-continuously or a designated intervals as necessary. In another embodiment, the biocide can be added batch-wise to shock-treat the system.

According to another embodiment, the biocide may be combined with the aqueous hydrogen peroxide 122 in its source container 124 and added to the recycle line 116 with the aqueous hydrogen peroxide composition 122. In yet another embodiment, the biocide may be combined with the acid or base 138 in its source container 150 and added to the recycle line 116 with the acid or base 138. In another embodiment, the biocide may be combined with the decomposition additive 130 in its source container 132 and added to the recycle line 116 with the decomposition additive 130. Additional details describing the process of adding the biocide are discussed in below. The biocide may also be added directly to the sump 112. The biocide is added in the various methods described above as an aqueous solution. In other embodiments, a tablet form of a biocide, such as bromide, is used and can be added directly to the sump 112. It should be appreciated that in those embodiments in which the biocide is combined with another material before being added to the recycle line 116 the biocide may be added directly to the respective source container of the other material or added to its own source container 152 and from there added through its feed line 156 to the appropriate other source container through separate feed lines 160, 162, 164.

Figure 2:
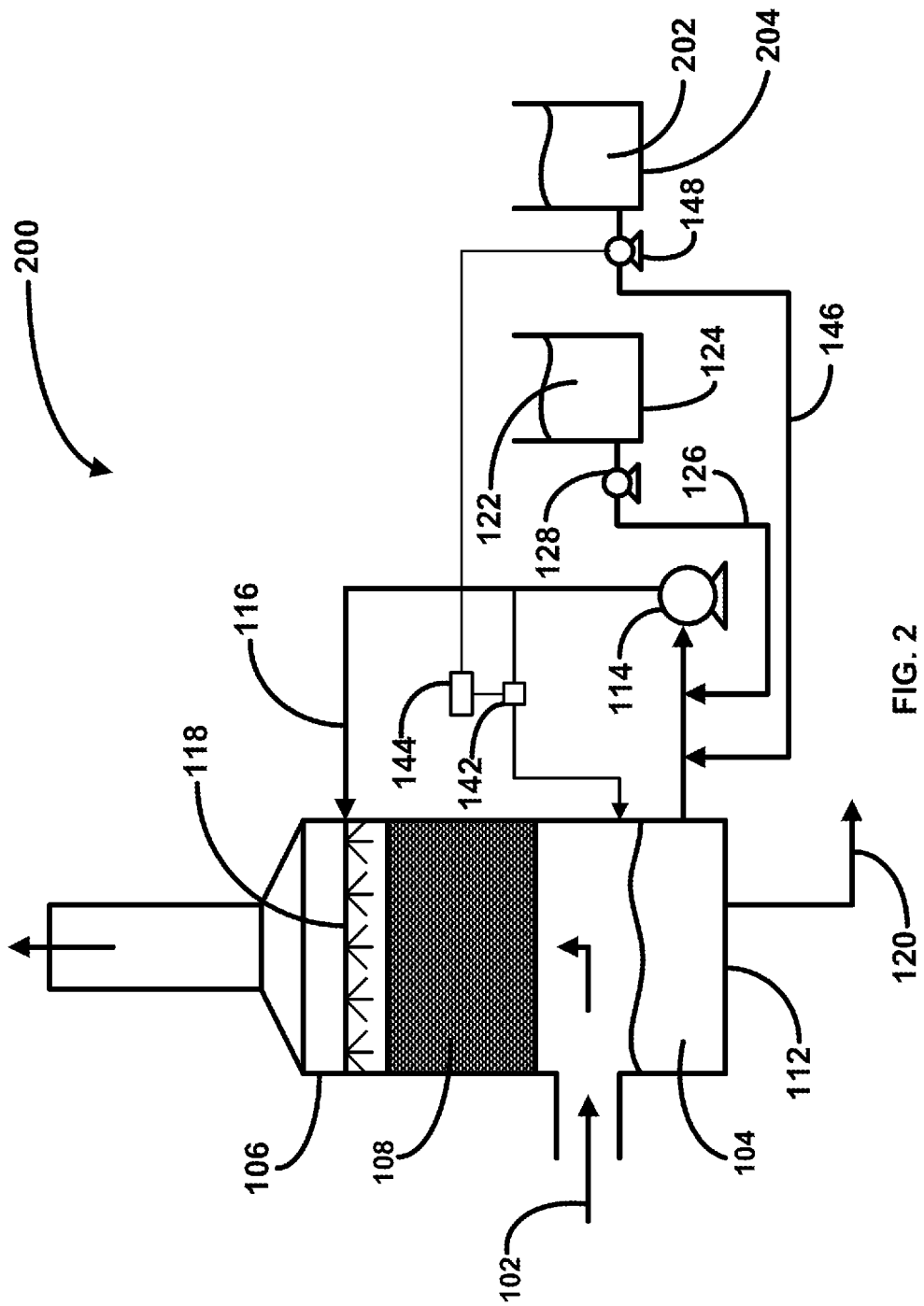
FIG. 2 shows a process flow diagram of another embodiment of a process for removing an odor and/or noxious component from a gas stream and for reducing biological fouling in the process.

FIG. 2 shows a process flow diagram of another embodiment of a process for removing an odor and/or noxious component from a gas stream and for reducing biological fouling in the process. This process 200 is similar to that shown in FIG. 1; however, in this case the decomposition additive, acid or base, and the biocide are combined 202 in one source container 204. The additive, acid or base, and biocide are delivered to the recycle line 116 through a feed line 146 using a pump 148. In this case, these materials 202 are delivered upstream of the recycle pump 114 and the hydrogen peroxide 122 is delivered downstream of the point where these materials 202 are added to the recycle line 116 but also upstream of the recycle pump. It should be appreciated, however, that the hydrogen peroxide 122 may also be added downstream of the recycle pump 114.

As described above in connection with FIGS. 1 and 2, a biocide is added to the scrubber 106 to treat biofouling that may occur in the scrubber 106, particularly in the packing 108 or in the sump 112. According to one embodiment, the amount of biocide added is the amount necessary to maintain a residual concentration in the scrubbing solution 104. Depending upon the biocide used, manufacturer's recommendations for the amount of biocide necessary may also be used. Further, certain operating parameters can be measured to determine whether the amount of biocide added or the concentration of biocide needs to be altered. For example, one technique for determining whether an accumulation of biofouling exists in the scrubber 106 is by monitoring the gas pressure differential across the packing 108. A drop in the gas pressure across the packing 108, or an increase in the gas differential, may be used to indicate an increase in biofouling in the packing 108 that increases the pressure drop across the packing 108. In this case, additional biocide may be added or the residual biocide concentration may be increased.

Generally, any biocide may be used. In one embodiment, the biocide is quaternary ammonium. In some embodiments, the residual concentration of quaternary ammonium in the scrubbing solution is about 6 to about 7 parts per billion (ppb). In another embodiment, the biocide is not an oxidizer. Such non-oxidizers include dibromo nitrilopropionamide (DBNPA), 2,2 Dibromo-3-nitrilopropionamide, gluteraldehyde, a carbamate, mercaptobenzothiazole (MBT), or isothiazolinone. In some embodiments, the biocide is a mixture of alkyl dimethylbenzylammonium chloride and alkyl dimethylethylbenzyl-ammonium chloride, including, in some embodiments, a mixture of these two compounds at 25% by weight.

It should be appreciated that the addition rates of any of the foregoing materials to the recycle line 116, the sump 112, or to the scrubbing solution 104 in general can be regulated to achieve the desired feed rate and concentration in the scrubbing solution 104 by any means known in the art, such as control valves, flow meters, or variable speed pumps. Further, the equipment for feeding these components may by stand-alone or independent or be incorporated as part of a larger control system, particularly in the case where the system includes more than one scrubber. It will be appreciated that other embodiments may be utilized in which the components of the scrubbing solution 104 are added at different locations within the system, including different locations along the recycle line 116 or directly to the sump 112.

One of skill in the art will appreciate that the actual composition of the scrubbing solution in the recycle line and, specifically, the concentration of hydrogen peroxide, the decomposition additive, and hydroxyl free radicals therein, is determined based upon the composition of the gas stream entering the scrubber and the specific gaseous components to be removed, as well as the scrubber operating conditions. At a given set of scrubber operating conditions (such as the gas flow rate and concentration of odorous and/or noxious components and the scrubbing solution flow rate through the scrubber), the addition rate of either or both of the hydrogen peroxide and the decomposition additive may be adjusted to provide the necessary production of hydroxyl free radicals to achieve the desired removal rate of odorous and/or noxious components. Of course, the concentration of the hydrogen peroxide and the decomposition additive in their respective source containers may be adjusted to achieve the desired rate of addition of each to the system taking into account overall water balance considerations.

The various embodiments described above have been primarily with reference to removal of odorous and/or noxious components from a gas stream in which the odorous and/or noxious components are absorbed and oxidized during contact with a scrubbing solution comprising hydrogen peroxide and hydroxyl radicals to produce a substantially non-odor offensive, environmentally acceptable byproduct. It should be appreciated, however, that various oxidizers or solutions containing oxidizers may be used. For example, oxidizing compounds such as chlorine gas, sodium hypochlorite, hypobromous acid, chlorine dioxide, hydrogen peroxide, peroxy acids, ozone, and permanganate may be used.

In addition, various embodiments have been described above in the context of the use of a wet scrubber system using a single packed column with a single integrated sump. It should be appreciated that other gas/liquid contactors may be used in the wet scrubber system. For example, spray towers, Venture spray condensers, or a combination of spray towers and packed columns may be used. Further, countercurrent scrubbers, where the direction of the gas flow is opposite the direction of the liquid flow; co-current scrubbers, where the direction of the gas flow is in the same direction as the liquid flow; and cross-flow scrubbers, where the direction of the gas flow is at an angle to the direction of the liquid flow; may be used. In addition, it should be appreciated that more than one sump may be used for a single scrubber or, alternatively, one sump may be used for more than one scrubber. Further, it should be appreciated that the sump does not necessarily need to be integral to the gas/liquid contactor and may be a separate tank, provided that appropriate gas seals are in place.

It should also be appreciated that more than one gas/liquid contactor may be used in a single system. Such gas/liquid contactors may be of the same or various types and may be configured to operate in series or in parallel. Each gas/liquid contactor could also have its own reservoir or multiple gas/liquid contactors may share the same sump. In using more than one gas/liquid contactor with one or more sumps, it is possible to utilize one set of source containers for hydrogen peroxide, additives, and any acid or base required for pH control.

Figure 3:
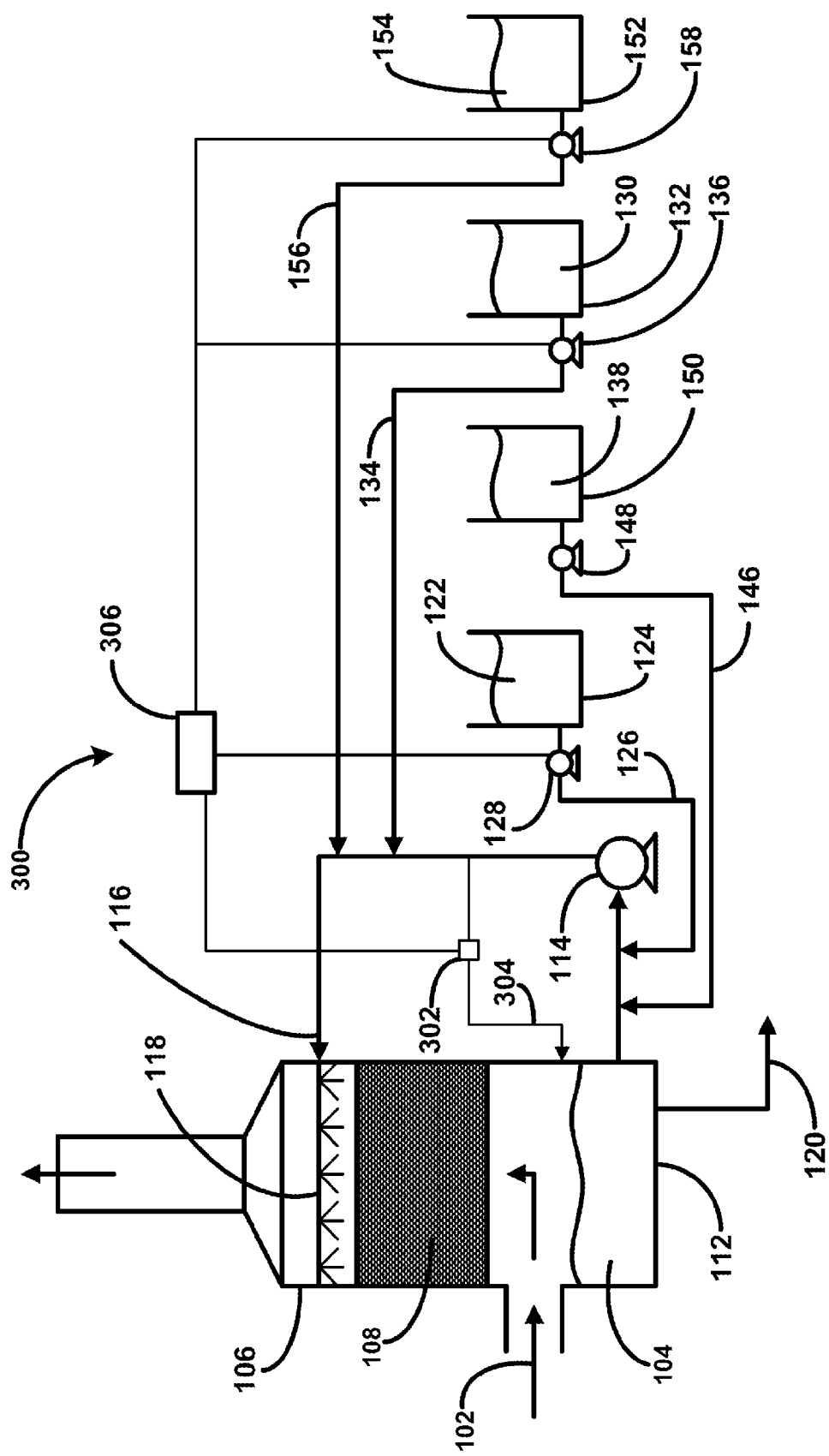
FIG. 3 illustrates a control system for the system of FIG. 1 or 2.

FIG. 3 illustrates a control system for the system of FIGS. 1 and 2. As noted above, the addition of the hydrogen peroxide and the decomposition additive, as well as other additives, is regulated to provide the desired composition in the scrubbing solution in the scrubber. Similar to the pH control loop discussed above in connection with FIG. 1, FIG. 3 illustrates a probe 302 that is designed to measure a given solution parameter or measurable parameter that can be used to control the addition rate of the hydrogen peroxide, the other additives or both. For example, the probe 302 may measure the oxidation-reduction potential of the solution or a particular chemical species, such as a given additive, a species that is indicative of the concentration of the additive, the concentration of gaseous species absorbed by the scrubber, or a combination of these. This probe 302 may be placed in a sidestream 304 similar to the one described above in connection with the pH probe 142. A controller 306 may be used to receive the output from the probe 302 and in response automatically control the addition rate of either the hydrogen peroxide 122 in source container 124, the decomposition additive 130 in source container 132, or the biocide 154 in source container 152 or the addition rate of all of these by controlling their respective feed pumps 128, 136, 158. In one embodiment, the hydrogen peroxide addition rate may be set at a given, constant value, and the probe 302 and controller 306 would be used to control the addition rate of the decomposition additive 130. Alternatively, the rate of addition of the decomposition additive 130 may be set at a given, constant value, and the probe 302 and controller 306 would be used to control the addition rate of the hydrogen peroxide 122. Similarly, the biocide addition rate may be set at a given, constant value, and the probe 302 and controller 306 would be used to control the addition rate of the decomposition additive 130. It should be appreciated, that separate control loops may be used for the hydrogen peroxide 122 and the decomposition additive 130, respectively, depending upon the type of probe used and the solution parameter that is being measured. It should also be appreciated that the above described controls may be used in combination with the pH control loop previously described in connection with FIG. 1 for the addition of an acid or base 138.

Figure 4:
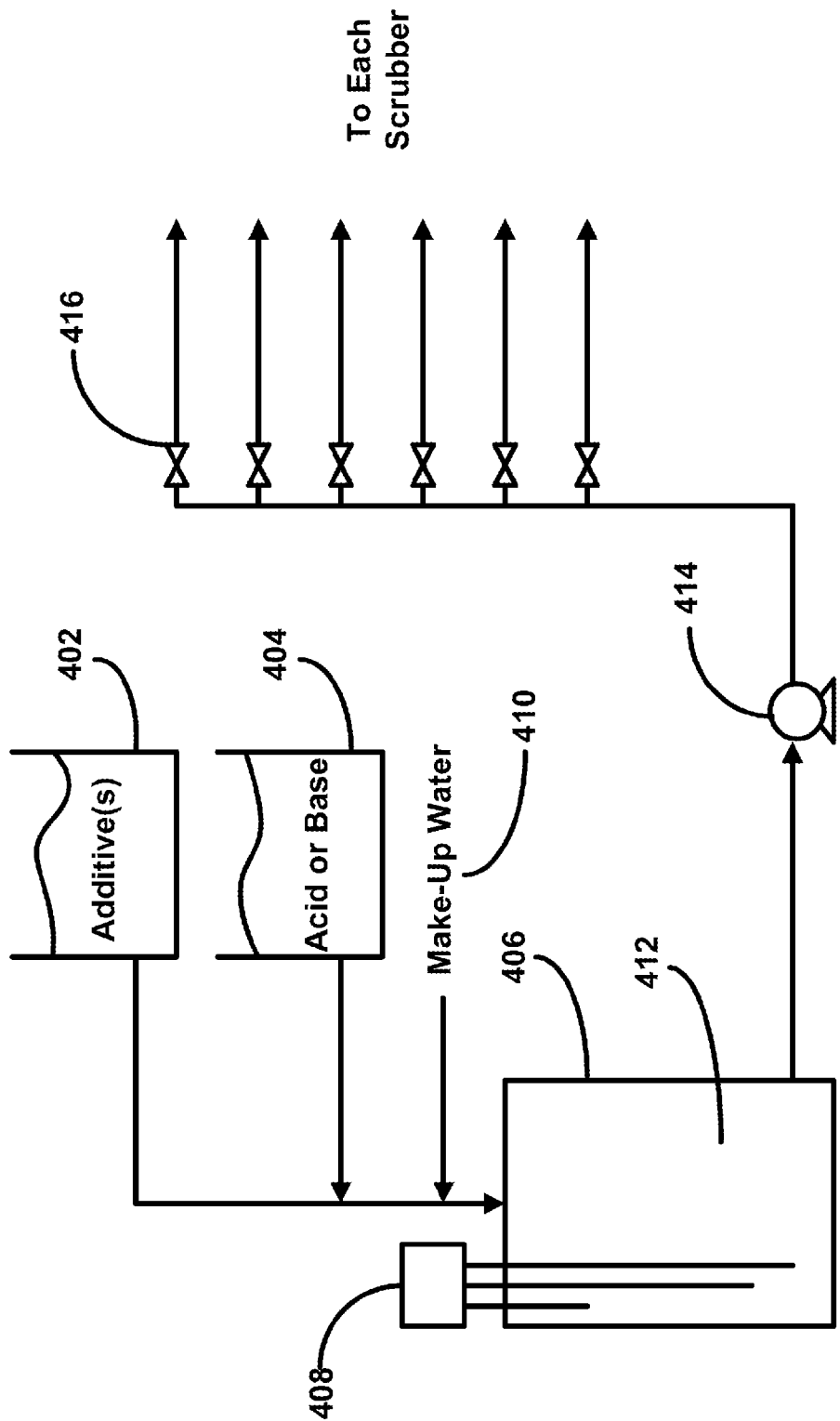
FIG. 4 illustrates a flow diagram for a system for adding additives, such as the decomposition additive and other additives described above, including a biocide, and acid or base for pH control to one or more gas/liquid contactors or scrubbers.

FIG. 4 illustrates a flow diagram for a system for adding additives, such as the decomposition additive and other additives described above, including a biocide, and acid or base for pH control to one or more gas/liquid contactors or scrubbers. As noted above, a system for treating a gas stream containing odorous and/or noxious components may include more than one scrubber/sump combination. In the configuration shown in FIG. 4, each source container for each additive 402 and for acid or base 404 (e.g., a ferrous sulfate source container and a source container for acid or base for pH control) is fluidly connected to a single feed tank 406. The feed tank 406 may have a level controller 408 that is used to control the addition rate of the additive(s), the acid or base, make-up water 410, or a combination of these to the feed tank 406. Of course, the concentration of the additive(s) and acid or base in their respective source containers 402, 404 will need to be accounted for in determining their addition rate to the feed tank 406 or vice versa. It should be appreciated that while FIG. 4 is shown for use in adding additives and acid or base to multiple scrubbers, the use of a single tank 406 for mixing additives and acid or base may be used for systems having only one scrubber/sump as well.

The feed tank 406, accordingly, comprises a solution 412 of the various additives fed to it and any desired acid or base for pH control of the scrubbing solution for each scrubber. Depending upon the additive or combination of additives used, the chemical effect of the addition of acid or base to the feed tank 406 on any such additives needs to be considered to ensure that the desired chemical effect of the additives would not be adversely altered before its addition to the scrubbers.

The feed tank 406 is fluidly connected to a distribution pump 414 that is fluidly connected to each scrubber's recycle line at the desired location along each recycle line. One desired location for distributing the solution 412 from the feed tank 406 to each recycle line of each scrubber may be downstream of each scrubber's recycle pump. It should be appreciated, however, that the point of addition to each scrubber may vary from scrubber to scrubber and may include points other than the recycle line or other locations along the recycle line. In other words, the solution 412 may be added to different locations along each scrubber's recycle line or at different points for each scrubber, such as each scrubber's sump.

It should be appreciated that flow control valves 416 may be used to control the flow rate of the solution 412 in the feed tank 406 to each scrubber. Any flow control valve, including a valve having precise control over the flow rate that passes through it, such as an analog valve, or, alternatively, an on/off valve may be used depending upon the method and amount of control desired. In either case, the flow control valves 416 may be controlled based upon a certain solution parameter measured, either on a continuous, semi-continuous or periodic, or manual basis, in each scrubber's recycle line or in each scrubber's sump. The solution parameter measured may be the concentration of any chemical species or solution specific measurement that provides information that can be used to determine whether to add additional additive(s). The solution parameter may include such parameters as pH, oxidation reduction potential, the concentration of the decomposition additive or a particular chemical species indicative of the concentration of the additive, the concentration of gaseous species absorbed by the scrubber, or a combination of these as further described below. In some embodiments, the measurement of the solution parameter is done automatically either on a continuous, semi-continuous or periodic basis, and the results of such measurement are used to automatically control the flow control valve 416. Of course, the required feed rate of the solution 412 in the feed tank 406 to each scrubber will be based upon each particular application, including, for example, the particular noxious components to be removed, the amount of gas being treated, and the operating conditions of each scrubber (e.g., the recirculation rate of the scrubbing solution through the scrubber) and the concentration of the various components in the solution 412 in the feed tank 406.

In operation, the addition rate of the solution 412 from the feed tank 406 to each recycle line of each scrubber may be controlled in various manners. In some embodiments, the addition of this solution 412 is controlled by the pH control loop on each recycle line as described above in connection with FIG. 1. In this case, a separate pH controller would be used for each scrubber and would control a respective flow control valve 416 to determine the flow rate of solution 412 from the feed tank 406 to that scrubber's recycle line. In other embodiments, different solution parameters could be monitored and used to control the addition rate of the solution 412 from the feed tank 406 by each flow control valve 416. As noted above, oxidation reduction potential, the concentration of the decomposition additive or a particular chemical species indicative of the concentration of the additive, the concentration of gaseous species absorbed by the scrubber, or a combination of these could be monitored and used to control the addition rate of the solution 412 to each scrubber.

As described above, depending upon the specific application, the concentrations of the additive(s) and the acid or base in the solution 412 can be adjusted so that the appropriate amount of each is fed to each scrubber. In addition, the relative concentrations in the solution 412 in the feed tank 406 may need to be adjusted for each specific application so that the appropriate amount of each additive and acid or base can be fed to each scrubber. This can be accomplished by adjusted the concentration of the additives and the acid or base in their respective source containers 402, 404. Further, these concentrations must be adjusted to be consistent with each scrubber's and the overall system water balance.

It should be appreciated that using a flow control valve 416 allows for more precise control of the flow rate to each scrubber, as opposed to a simple on/off valve, in combination with monitoring either pH or another solution parameter provides for better control of the solution chemistry and removal of the noxious and odorous components. Particularly by monitoring the pH or another solution parameter in the recycle stream, as shown in FIGS. 1 and 3, the composition of the solution that is contacting the gas stream is better known than, for example, monitoring the solution in the sump. Further, by adding the additive and/or acid or base directly to the recycle line based upon the results of monitoring of the solution in the recycle line allows the recycle line chemistry to be properly controlled or adjusted just prior to entering the scrubber. This allows for more optimal control of the removal of the odorous and/or noxious components.

Optionally, any make-up water 410 required for each reservoir may also be added to the feed tank 406. In this case, the dilution effect of any water added to the feed tank 406 must be taken into account so that the desired amount of each additives and acid or base are ultimately added to each recycle line. In addition, the water make-up needs of each reservoir, to the extent that they are different, must be taken into account. In other words, a water balance must be achieved for the overall system, which will also impact the amount of water in the feed tank 406, as discussed above. Alternatively, make-up water 410 may be added directly to each scrubber's sump.

It should be appreciated as an alternative to FIG. 4 that the hydrogen peroxide can be added from separate source containers directly to the recycle line of each scrubber, or a single source container can be used with a distribution system to each recycle line of each scrubber. Preferably, the hydrogen peroxide would be added upstream of each scrubber's recycle pump. In all cases, a control valve would be used to monitor and regulate the flow of hydrogen peroxide to each scrubber. The control of such a control valve could be based upon the removal efficiency of each scrubber or it could be based upon the relative addition rate of the decomposition additive to the recycle line of each scrubber.

Further, it should be appreciated as an alternative to FIG. 4, each source container of additive or acid or base may be separately connected to a separate corresponding main header line that is fluidly connected to each recycle line of each scrubber at the desired location along the recycle line. In other words, the source container for each additive would be separately connected to each scrubber via its own main header line. As described above, one desired location for the addition of additives that catalyze the decomposition of hydrogen peroxide to each scrubber may be downstream of each scrubber's recycle pump. It should be appreciated, however, that the desired location for the addition of other additives may vary according to the particular additive used. For example, as described above, in using ozone as the catalyst, an air/ozone mixture may be added directly to a regenerative turbine pump in the recycle line of each scrubber. Alternatively, a regenerative turbine pump may be used to pump hydrogen peroxide from its source container to a main header line that is fluidly connected to each scrubber, wherein an air/ozone mixture is added to that regenerative turbine pump rather than to each pump in each recycle line.

Desired locations for the addition of acid or base for pH control in this alternative embodiment include upstream of each scrubber's recycle pump and in some embodiments upstream of the addition point for the hydrogen peroxide. In this alternative, the hydrogen peroxide may be added, for example, in the same manner as described above in connection with FIG. 4.

Generally, it should be appreciated that the addition of the various components comprising the aqueous hydrogen peroxide composition may be added at various locations throughout the scrubber system and are not limited to those described in the above embodiments. For example, the hydrogen peroxide and other additives may be added at other locations in the recycle line or directly to each scrubber's sump, although some of these locations are more desirable than others, as discussed in the embodiments above.

Figure 5:
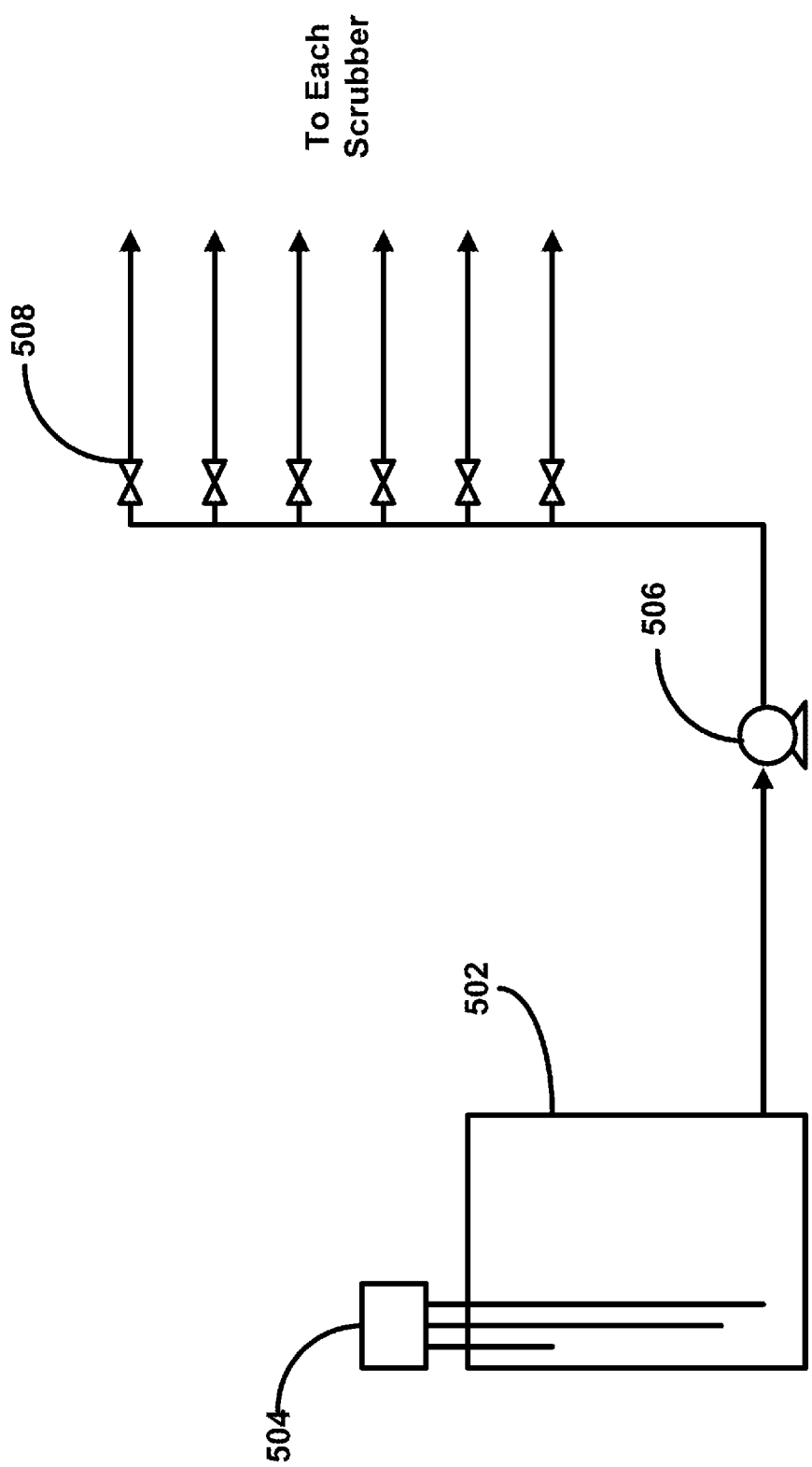
FIG. 5 illustrates a flow diagram for a system for adding an oxidizer to one or more gas/liquid contactors or scrubbers.

FIG. 5 illustrates a flow diagram for a system for adding an oxidizer to one or more gas/liquid contactors or scrubbers. A feed tank 502 is used to hold the oxidizer, which may include hydrogen peroxide or another oxidizer such as chlorine gas, sodium hypochlorite, hypobromous acid, chlorine dioxide, hydrogen peroxide, peroxy acids, ozone, and permanganate. The feed tank 502 may also have a level controller 504 that functions to provide an alert when the tank level is low and additional hydrogen peroxide and/or water is required. It should be appreciated that certain additives, including any of the additives described such as a biocide (with the exception of a decomposition additive if hydrogen peroxide is used as the oxidizer) may also be added to the feed tank 502 provided they are chemically compatible with an oxidizer, such as hydrogen peroxide, so that their chemical activity is not lost prior to being added to the scrubber. It should also be appreciated that the system of FIG. 5 can be used in conjunction with the system of FIG. 4 and further in conjunction with a pH control loop.

The feed tank 502 is fluidly connected to a distribution pump 506 that is fluidly connected to each scrubber's recycle line via a flow control valve 508 at the desired location along each recycle line. One desired location for distributing the oxidizer from the feed tank 502 to each recycle line may be upstream of each scrubber's recycle pump. It should be appreciated, however, that the point of addition to each scrubber may vary from scrubber to scrubber and may include points other than the recycle line or other or additional points along the recycle line. In other words, the oxidizer may be added to different locations along each scrubber's recycle line or at different points for each scrubber, such as each scrubber's sump.

In operation, the addition rate of the oxidizer from the feed tank 502 to each recycle line of each scrubber may be controlled in various manners. In some embodiments, the addition of the oxidizer is simply set a given feed rate for each scrubber using the flow control valve 508. In other embodiments, different solution parameters could be monitored and used to control the addition rate of the oxidizer from the feed tank 502 by the flow control valve 508. As noted above, oxidation reduction potential, the concentration of the decomposition additive or a particular chemical species indicative of the concentration of the additive, the concentration of gaseous species absorbed by the scrubber, or a combination of these could be monitored and used to control the addition rate of the oxidizer from the feed tank 502. Of course, the concentration of the oxidizer will need to be accounted for in determining its addition rate to each scrubber or vice versa.

It should be appreciated that using a flow control valve 508 allows for more precise control of the flow rate to each scrubber, as opposed to a simple on/off valve. Particularly, by monitoring a given solution parameter in the recycle line the composition of the solution that is contacting the gas stream is better known than, for example, monitoring the solution in the sump. Further, by adding the oxidizer directly to the recycle line based upon the results of monitoring of the solution in the recycle line allows the recycle line chemistry to be properly controlled or adjusted just prior to entering the scrubber. This allows for more optimal control of the removal of the odorous and/or noxious components. However, it should be appreciated that in one embodiment it is desirable to simply set the addition rate of the oxidizer to a given, constant value and to adjust the addition rate of any additives (e.g., a decomposition additive in the case of using hydrogen peroxide as the oxidizer) accordingly.

Optionally, any make-up water required for each reservoir may also be added to the feed tank 502 (not shown). In this case, the dilution effect of any water added to the feed tank 502 must be taken into account so that the desired amount of each additives and acid or base are ultimately added to each recycle line. In addition, the water make-up needs of each sump, to the extent that they are different, must be taken into account. In other words, a water balance must be achieved for the overall system, which will also impact the amount of water in the feed tank 502, as discussed above. Alternatively, make-up water may be added directly to each scrubber's sump.

As mentioned above, liquid discharged from each scrubber's sump, as shown, for example, in FIG. 1 by the discharge line 120, also offers advantages as in influent to the wastewater treatment process. For example, when using ferrous sulfate as the additive to catalyze the decomposition of the hydrogen peroxide, the discharge from each scrubber's sump can be passed to a wastewater treatment facility, for example, by dumping the entire liquid content of the sump or by continuous overflow from the sump or recycle line, and this stream will have been effectively "pretreated" by cationic ferric hydroxide complexes that offer effective colloidal charge neutralization as well as the ability to adsorb wastewater constituents into its floc matrix. The addition of a charge neutralizing/adsorption species is always an added cost at the wastewater treatment plant, which may be accordingly be eliminated or greatly reduced.

Figure 6:
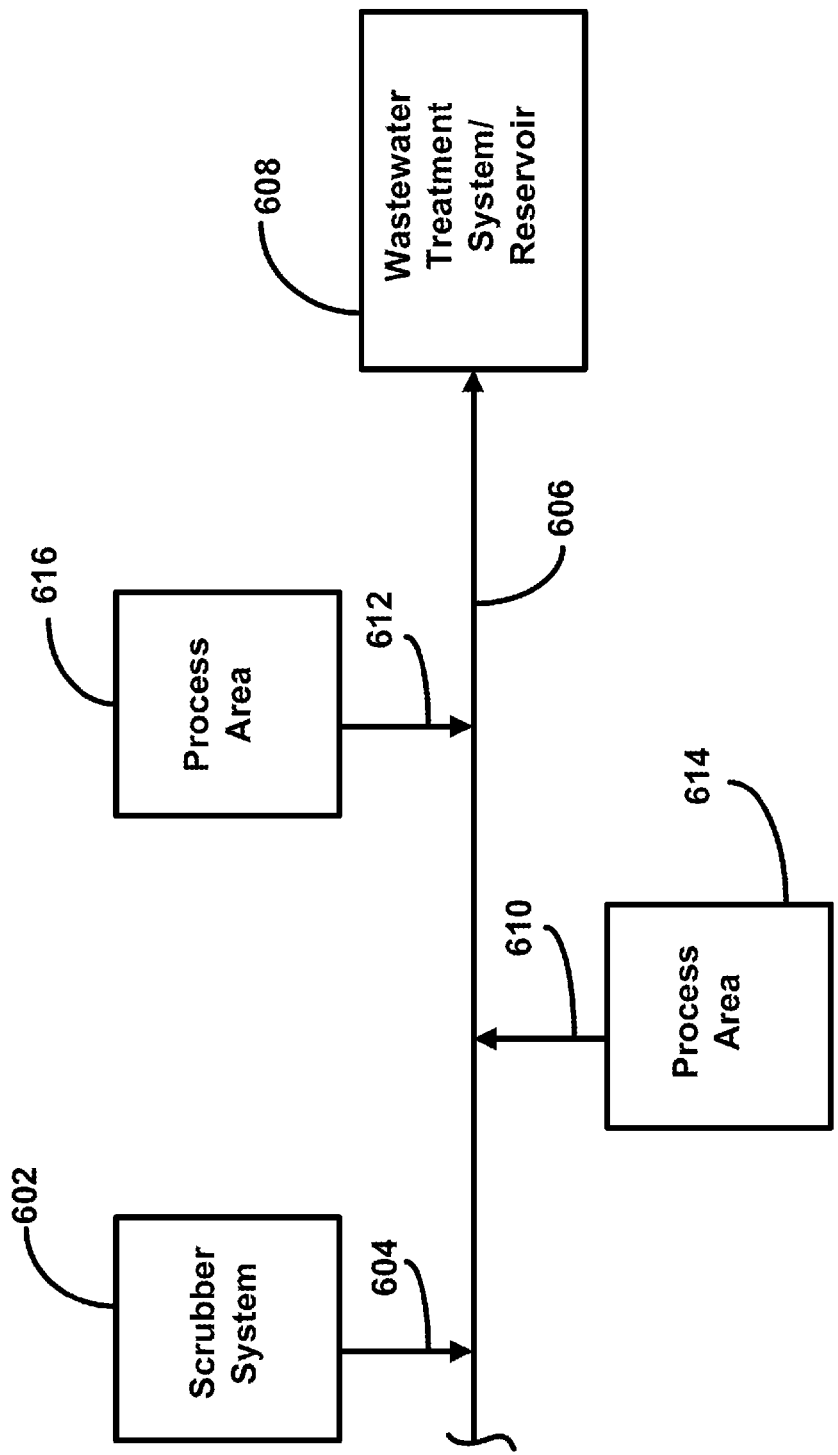
FIG. 6 illustrates a flow diagram for the connection between a scrubber system and a wastewater treatment system.

FIG. 6 illustrates a flow diagram for the connection between a scrubber system and a wastewater treatment system. FIG. 6 illustrates a scrubber system 602 according to any of the embodiments described above. Liquid discharge 604 from the scrubber system 602, such as liquid discharge 120 shown in FIG. 1, is passed by a common wastewater line 606 to a wastewater treatment facility 608. As earlier described, the liquid discharge from the scrubber system 602 may include an entire dump of the scrubber sump or may be a continuous overflow of liquid from the scrubber sump, depending upon operating conditions.

Wastewater 610, 612 from other process areas 614, 616 of the plant, such as wash and rinse waters, chicken feather processing waters, rendering cooker waters, etc., may also be added to the common wastewater line 606. All of the wastewaters added to the common wastewater line 606 are sent to the wastewater treatment facility 608 where the wastewaters are treated as necessary.

When the wastewater enters the wastewater treatment facility 608, however, the wastewater is effectively "pretreated" as the discharge from the scrubber sump may contain metal hydroxide complexes, for example, cationic ferric hydroxide complexes, that offer effective colloidal charge neutralization, as well as provide for adsorption of wastewater constituents into its floc matrix. While some of the complexes are utilized by the components of the discharge from the scrubber system 604, a residual amount of these complexes are also available to react with components in other wastewaters 610, 612 combined with the discharge from the scrubber 604. As wastewater treatment facilities typically purchase additives to accomplish these results, the addition of these charge neutralizing and adsorption species eliminates or greatly reduces any costs incurred by the waste treatment facility 608.

The present invention has been described above with reference to removal of odor and/or noxious components from an atmospheric effluent in which the oxidized odor and/or noxious components are oxidized during contact with an aqueous hydrogen peroxide composition to produce a substantially non-odor offensive, environmentally acceptable byproduct that is solubilized in or adsorbed onto the aqueous hydrogen peroxide composition to form a liquid effluent, and the advantages of such a system provided to wastewater treatment processes. The present invention also has application in other areas of processing plants as an effective biocide, especially in areas related to aqueous food transport flumes.

Food primary and secondary processing involves the handling of large amounts of organic materials. As a result of the amount of organics being processed, biological activity is inevitable. In fruit and vegetable processing, large amounts of water are used to wash and transport food through the various processing steps. Because of the buildup of organic matter, the transport and wash waters are very prone to biological growth, as well as accumulation of toxic organic materials such as herbicides and pesticides. A need exists to provide microbial control of these waters without imparting further toxic products to the aqueous food contact streams. Also needed is an economical method for eliminating or reducing the buildup of toxic herbicides and pesticides in the food transport system.

Attempts in the art have been made utilizing oxidizing compounds such as chlorine gas, sodium hypochlorite, hypobromous acid, chlorine dioxide, hydrogen peroxide, peroxy acids, ozone, and permanganate. While some are effective in limiting microbial growth, either toxic byproducts, cost, or inefficiencies are limiting factors.

Particularly, the use of chlorine and chlorine dioxide, while effective antimicrobial agents, has come under environmental scrutiny due to the toxic byproducts it produces. When contacted with amines, toxic chloramines are formed, as well as trihalomethane compounds, which are now prevalent in most ground waters in the United States. Chlorine-based technologies also use large quantities of these materials, as they are rapidly consumed by the high organic loading of the aqueous media before they can impart antimicrobial properties. Hypobromous acid produced by the decomposition of sodium bromide by chlorine has been used with some success, but it too is affected by high organic loading and the chlorine substrates, which, while reduced, still impart the same toxicities as hypochlorous acid.

Hydrogen peroxide has been used with limited success. Hydrogen peroxide is a slow reacting compound with known antimicrobial properties. The reaction rates are too slow for effective, cost advantageous microbial control. Peroxy acids such as peracetic acid have proven to be effective antimicrobial compounds in aqueous systems. Peracids are usually manufactured by the combination of hydrogen peroxide, acetic acid, and inorganic acid catalyst, and various wetting and sequestering agents. Peracetic acid is normally provided in 5 to 15% peracetic acid concentrations. These peracid compounds contain large amounts of the manufacturing precursors, such as hydrogen peroxide, and acetic acid. These peroxy acid materials have a strong pungent odor and residual acetic acids are toxic by ingestion or exposure at 10 ppm in misted form. Peroxy acids are also limited in use by the high costs that are associated with it. Ozone has found limited use in aqueous food transport and processing streams. Ozone is an effective biocide and its high electronegativity is capable of breaking down selected organic compounds. Ozone is associated with extremely high capital investments cost, and the efficiency is limited by poor transfer coefficients from the generated ozone gas phase to the liquid media being treated.

Use of the present invention, however, in which an aqueous hydrogen peroxide composition of hydrogen peroxide decomposed by ozone is contacted with the transport waters, results in an effective biocide. This allows sterilization of food transport waters with no toxic byproducts. Further, in food transport flumes, regulation of the ozone can also break down accumulated pesticide and herbicide compounds from fruit and vegetable washing into simple non-toxic carboxylic acids. Accordingly, this technology offers significant cost and efficiency advantages over current technologies.

EXAMPLES

The following examples describe specific aspects of the present invention to illustrate the invention and aid those of skill in the art in understanding and practicing the invention. The examples should not be construed as limiting the present invention in any manner.

Example #1

A 1000 ml sample of chicken feather processing scrubber water having a pH of 5.5 due to sulfuric acid addition in the scrubber reservoir was evaluated. The sample had an intense odor after treatment with chlorine dioxide. The sample was treated concurrently with 300 ppm of hydrogen peroxide (50% solution) and 100 ppm ferrous sulfate (38% solution). The reaction was instantaneous, and there was no detectable odor, other than a slight chlorine smell.

Example #2

A 1000 ml sample from a rendering cooker was adjusted to pH 5.5 with sulfuric acid. The sample had a very intense odor. The sample was treated concurrently with 300 ppm of hydrogen peroxide (50% solution) and 100 ppm ferrous sulfate (38% solution). The reaction was instantaneous, and the odor was eliminated within 15 seconds. The sample was then undisturbed for 48 hours, and there was no re-occurrence of any odor.

Example #3

A five gallon sample from a rendering cooker was adjusted to pH 5.5. The sample was recirculated at 10 gpm through a Burks regenerative turbine pump throttled by pinch valve assembly to 100 psi. Hydrogen peroxide was introduced into the suction line at 300 ppm. Ozone as a 6% gas stream generated by a corona discharge type ozonater on dried air was added into the air inlet for the Burks pump (suction side). The ozone dose was 10 ppm as ozone. The sample was recirculated for 2 minutes, and odors were completely neutralized. The sample was then un-aerated and undisturbed for 48 hours, and there was no re-occurrence of any odor.

Example #4

A trial was performed at a mixed proteins rendering plant that used chlorine dioxide in a scrubber to reduce VOC emissions by 88%. In this system, the pH was reduced to pH 5.5 with sulfuric acid. 300 ppm of hydrogen peroxide (50% solution) and 100 ppm ferrous sulfate (38% solution) were added concurrently. As a result, VOC emissions were reduced by 96%.

In the above examples, odor reduction was measured using the sense of smell and VOC emission measurements using standard emission detectors. It will be appreciated that various other devices and measurement techniques may also be used that conform to standard practices as may be required for a particular processing industry.

Example #5

A pilot plant test using hydrogen peroxide decomposed by ozone was conducted to evaluate microbiological control. The test or run was performed using 100 gallons and a Pennsylvania apple wash/transport flume with the following characteristics: BOD=900 ppm, COD=2100 ppm, and a significant amount of large organic matter. The material was recirculated for 36 hours and the following data was collected: bio count via dip slide=109, filtered BOD (0.45 micron)=685 ppm, filtered COD (0.45 micron)=1725 ppm.

300 ppm hydrogen peroxide (50% solution) was added, and ozone was added at 10 ppm into a regenerative turbine pump used to recirculate solution. When the addition of hydrogen peroxide and ozone was completed the addition was stopped. The following bio count in colonies was observed: @ t=4 min bio count=102, @ t=10 min bio count=none detected, @ t=8 hours bio count=none detected, @ t=12 hours bio count=10, and @ t=18 hours bio count=102. Additional data included: filtered BOD=210 ppm and filtered COD=720 ppm.

As can be seen by this test, microbial control was excellent with good sustained kill of biopopulation. The lowering of the COD showed decomposition of organic material in the sample water. Analysis for toxicity indicated a sharp drop.

What is claimed is:

1. A method for removing an odorous or noxious component from a gas stream, comprising:

adding hydrogen peroxide, a hydrogen peroxide decomposition additive, and a biocide to a liquid stream, wherein said biocide is added in an amount sufficient to eliminate biological fouling on at least one surface in a gas/liquid contactor, and wherein said liquid stream has a pH of less than 7;

contacting a gas stream comprising at least one odorous or noxious component with said liquid stream in the gas/liquid contactor having a pressure drop across the gas/liquid contactor;

absorbing at least a portion of said odorous or noxious component in said gas stream into said liquid stream; and eliminating biological fouling on at least one surface in the gas/liquid contactor during said contacting and said absorbing, thereby killing substantially all microorganisms on said at least one surface and thereby reducing the pressure drop across the gas/liquid contactor.

2. The method of claim 1, wherein the gas/liquid contactor comprises packing, wherein said eliminating biological fouling comprises eliminating biological fouling in the packing, and thereby reducing a pressure drop across the packing.

3. The method of claim 1, wherein the biocide comprises dibromo nitrilopropionamide.

4. The method of claim 1, wherein the biocide comprises gluteraldehyde.

5. The method of claim 1, wherein the biocide comprises a carbamate.

6. The method of claim 1, wherein the biocide comprises mercaptobenzothiazole.

7. The method of claim 1, wherein the biocide comprises isothiazolinone.

8. The method of claim 1, wherein the biocide comprises quaternary ammonium.

9. The method of claim 1, wherein said liquid stream comprises a residual concentration of the biocide.

10. The method of claim 1, further comprising:
controlling a pH of said liquid stream by adding acid or base to said liquid stream; and
mixing said acid or said base and said biocide to form a mixture of said acid or said base and said biocide prior to said adding of said hydrogen peroxide, said hydrogen peroxide decomposition additive, and said biocide to said liquid stream, and wherein said adding of said hydrogen peroxide, said hydrogen peroxide decomposition additive, and said biocide comprises adding said mixture of said acid or said base and said biocide.

11. The method of claim 1, wherein said adding comprises adding said hydrogen peroxide, hydrogen peroxide decomposition additive, and said biocide to said liquid stream concurrently.

12. The method of claim 1, wherein said adding comprises separately adding said hydrogen peroxide, said hydrogen peroxide decomposition additive, and said biocide to said liquid stream.

13. The method of claim 1, further comprising:
mixing said hydrogen peroxide and said biocide to form a mixture of said hydrogen peroxide and said biocide prior to said adding, and wherein said adding comprises adding said mixture of said hydrogen peroxide and said biocide.

14. The method of claim 1, further comprising:
mixing said hydrogen peroxide decomposition additive and said biocide to form a mixture of said hydrogen peroxide decomposition additive and said biocide prior to said adding, and wherein said adding comprises adding said mixture of said hydrogen peroxide decomposition additive and said biocide.

15. The method of claim 1, wherein said adding comprises adding a chelating agent to said liquid stream.

16. The method of claim 15, further comprising:
mixing said chelating agent and said biocide to form a mixture of said chelating agent and said biocide prior to said adding, and wherein said adding comprises adding said mixture of said chelating agent and said biocide.

17. The method of claim 1, wherein said contacting is performed in a gas/liquid contactor and further comprising:
monitoring biological fouling in said gas/liquid contactor.

18. The method of claim 17, wherein said monitoring comprises monitoring the gas pressure drop across the gas/liquid contactor.

19. The method of claim 18, further comprising:
adding additional biocide to said liquid stream in response to an increase in the gas pressure drop across the gas/liquid contactor.

20. A method for removing an odorous or noxious component from a gas stream, comprising:
adding hydrogen peroxide, a hydrogen peroxide decomposition additive, and a biocide to a liquid stream, wherein said biocide is added in an amount sufficient to prevent biological fouling on at least one surface in a gas/liquid contactor, and wherein said liquid stream has a pH of less than 7;
contacting a gas stream comprising at least one odorous or noxious component with said liquid stream in the gas/liquid contactor;
absorbing at least a portion of said odorous or noxious component in said gas stream into said liquid stream; and
preventing or eliminating biological fouling on at least one surface in the gas liquid contactor during said contacting and said absorbing, thereby killing substantially all microorganisms on said at least one surface.

21. A method for removing an odorous or noxious component from a gas stream, comprising:
adding hydrogen peroxide, a hydrogen peroxide decomposition additive, and a biocide to a liquid stream, wherein said biocide is added in an amount sufficient to stop all biological growth in the liquid stream, and wherein said liquid stream has a pH of less than 7;
contacting a gas stream comprising at least one odorous or noxious component with said liquid stream in a gas/liquid contactor;
absorbing at least a portion of said odorous or noxious component in said gas stream into said liquid stream; and
preventing biological growth in said liquid stream, thereby reducing the consumption of the hydrogen peroxide during said contacting and said absorbing.

* * * * *